United States Patent [19]

Hockenberry

[11] 4,446,726

[45] May 8, 1984

[54] APPARATUS AND METHOD FOR MEASURING THE FILTERABILITY OF A FLUID AT LOW TEMPERATURES

[75] Inventor: Richard L. Hockenberry, Viola, Ill.

[73] Assignee: Deere & Company, Moline, Ill.

[21] Appl. No.: 413,849

[22] Filed: Sep. 1, 1982

[51] Int. Cl.³ .............................................. G01N 33/26
[52] U.S. Cl. .................................... 73/61.4; 210/416.5
[58] Field of Search ..................... 73/61.4, 61 R, 38; 374/24, 17; 210/416 J, 416.4, 350

[56] References Cited

U.S. PATENT DOCUMENTS

| 3,872,710 | 3/1975 | Louvel | 374/24 |
| 4,181,009 | 1/1980 | Williamson | 73/61.4 |
| 4,397,177 | 8/1983 | Cain | 73/61.4 |

Primary Examiner—Gerald Goldberg
Assistant Examiner—James R. Giebel

[57] ABSTRACT

An apparatus and a method of measuring the filterability of a fluid which includes a cold box having a temperature regulating mechanism connected thereto. Enclosed in the cold box is a filter holder connected between first and second cylinders. The filter holder has a housing divided into two parts which are joined together by a quick attachment and release mechanism. The mechanism permits a calibrated filter to be inserted into or to be removed from the filter holder quickly and easily. The filter holder also has an inlet and an outlet with the inlet connected to the first cylinder and the outlet connected to the second cylinder. The first cylinder contains a free piston which separates a quantity of fluid which is present in one section of the cylinder from a pressurized inert gas which is supplied to an opposite side of the piston. By allowing the pressurized inert gas to impinge on the piston, the fluid is urged from the first cylinder through the calibrated filter. After passing through the filter, the fluid is conveyed to the second cylinder where it impinges on another free piston. The free piston in the second cylinder can be biased by gas pressure to a given position such that back pressure is created across the filter to simulate actual conditions which would occur in a full-size device, such as an engine. Such an apparatus and a method of using it permits the testing of lubricating oil within a laboratory environment.

14 Claims, 3 Drawing Figures

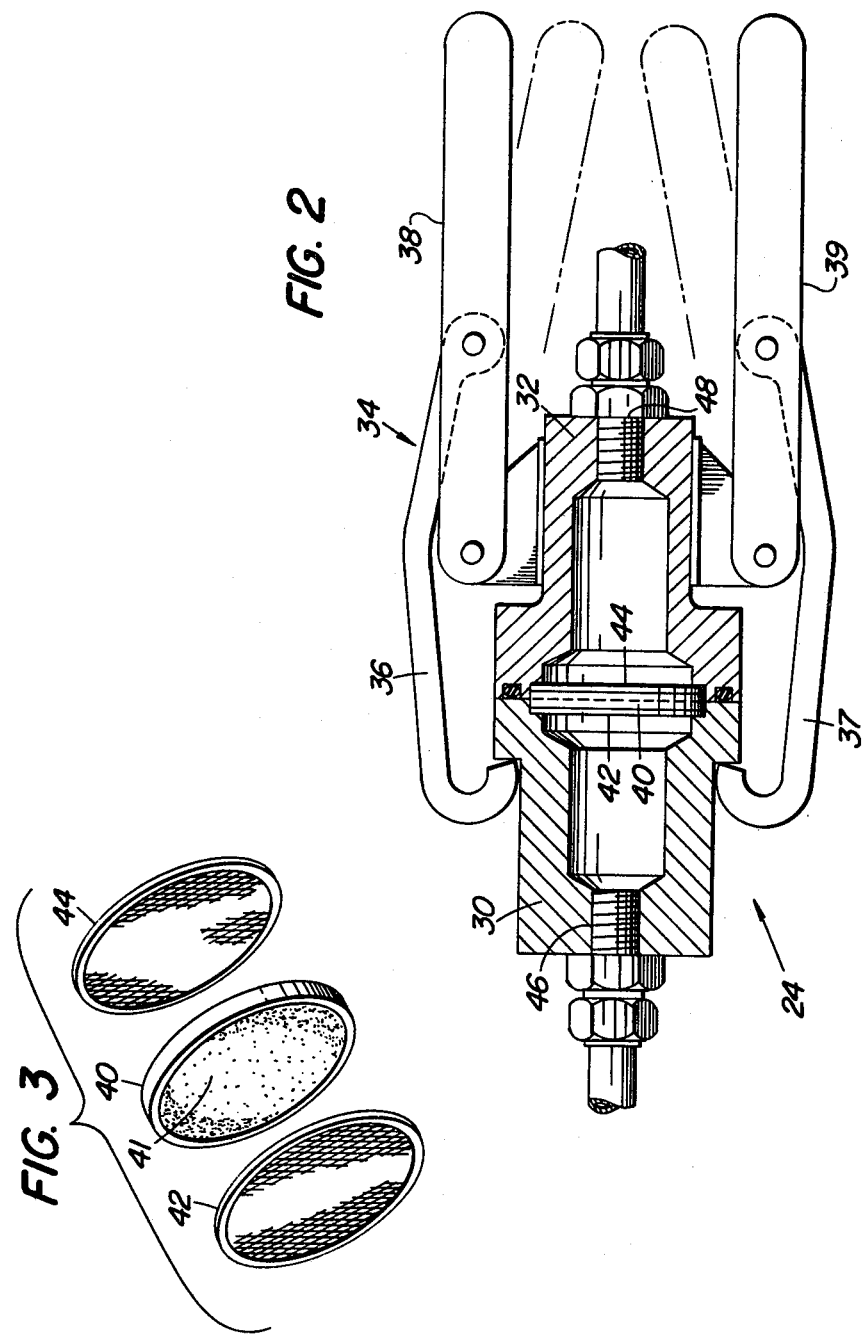

APPARATUS AND METHOD FOR MEASURING THE FILTERABILITY OF A FLUID AT LOW TEMPERATURES

FIELD OF THE INVENTION

This invention relates to an apparatus and a method for measuring the filterability of a fluid at low temperatures, and more particularly to an apparatus and method for measuring the filterability of a lubricating oil at low temperatures in a laboratory.

BACKGROUND OF THE INVENTION

Manufacturers of engines, transmissions and hydraulic devices have a need to test lubricating and hydraulic oils, in order to determine the flow and filterability characteristics of such oils as well as other parameters associated with the functional qualities, thereof. One way of so-testing these fluids is to use them in full size devices. However, for test purposes, this procedure is exceedingly expensive and requires an objectionably long period of time. In addition, when the oil to be tested is at a low temperature, it is necessary that the complete engine or vehicle be placed in a cold room and that the temperature be monitored over an extensive period of time in order to bring the lubricating oil to the required temperature of the test. In view of these disadvantages, it is desired to provide a relatively small, fast, simple-to-use laboratory apparatus wherein the oil can be rapidly tested under controlled conditions and with a high degree of correlation between the test results and the results that would be obtained when the oil is used in a full size device. Furthermore, it is desired that this apparatus be of a portable nature such that it can be readily transported to various locations in order to perform the test.

One attempt at providing a laboratory testing apparatus is disclosed in U.S. Pat. No. 3,872,710, entitled "Apparatus For Measuring the Index of Filterability of a Liquid". Structurally, this apparatus is different from the present invention in that it uses a regulating drum to supply fluid to a filter. The fluid, after passing through a filter, is routed to a reservoir or back into the regulating drum. There is no provision for creating a back pressure across the filter or for cooling the oil before it flows out of the regulating drum.

Now, an apparatus and method have been invented which will satisfy the present needs of the industry.

SUMMARY OF THE INVENTION

Briefly, this invention relates to an apparatus and a method for measuring the filterability of a fluid at low temperatures. The apparatus, which is designed to be inserted into a cold box having a temperature regulating mechanism connected thereto, includes a filter holder connected between first and second cylinders. The filter holder has a housing divided into two parts which are joined together by a quick attachment and release mechanism. The mechanism permits a calibrated filter to be inserted into or to be removed from the filter holder quickly and simply. The filter holder also has an inlet and an outlet, with the inlet being connected to the first cylinder and the outlet being connected to the second cylinder. The first cylinder contains a free piston which separates a quantity of fluid, which is inserted into the cylinder on one side of the piston, from a pressurized inert gas which is supplied to the opposite side of the piston. By allowing the pressurized inert gas to impinge on one side of the free piston, the fluid is urged out of the first cylinder and through the calibrated filter. After passing through the filter, the fluid is conveyed to the second cylinder wherein it impingers on another free piston. The free piston in the second cylinder can be biased to a given position by gas pressure such that a back pressure is created across the filter medium to simulate actual conditions which would occur in a device adapted to use the fluid being tested.

The apparatus also includes a flow meter positioned in the passage between the filter and the second cylinder so as to record the flow rate of the fluid. Furthermore, a number of control valves are positioned across the fluid passages to regulate the flow of the fluid through the apparatus. By measuring the quantity of fluid that is initially inserted into the first cylinder and by recording the rate of fluid flow, one is able to measure the filterability of the fluid through a filter of a given size at a given temperature.

The general object of this invention is to provide an apparatus and a method for measuring the filterability of a fluid at low temperatures. A more specific object of this invention is to provide an apparatus and a method for measuring the filterability of a lubricating oil at low temperatures in a laboratory environment.

Another object of this invention is to provide a portable apparatus which will measure the filterability of a lubricating oil or a hydraulic oil at low temperatures and which is simple in construction and economical to manufacture.

Still another object of this invention is to provide an apparatus for measuring the filterability of a fluid at low temperatures which simulates very closely the operating conditions of an actual device.

Still further, an object of this invention is to provide an apparatus which uses an inert gas to move a fluid at a low temperature through a calibrated filter such that no heat is imparted into the fluid as would be the case if a pump was used to circulate the fluid.

Other objects and advantages of the present invention will become more apparent to those skilled in the art in view of the following description and the accompanying drawings.

BRIEF DESCRIPTION OF THE DRAWINGS

FIG. 2 is a cross-sectional view of the filter holder having a calibrated filter positioned therein.

FIG. 3 is an assembly view of a filter having a screen positioned adjacent each side surface.

DETAILED DESCRIPTION OF THE PREFERRED EMBODIMENT

Figure 1:
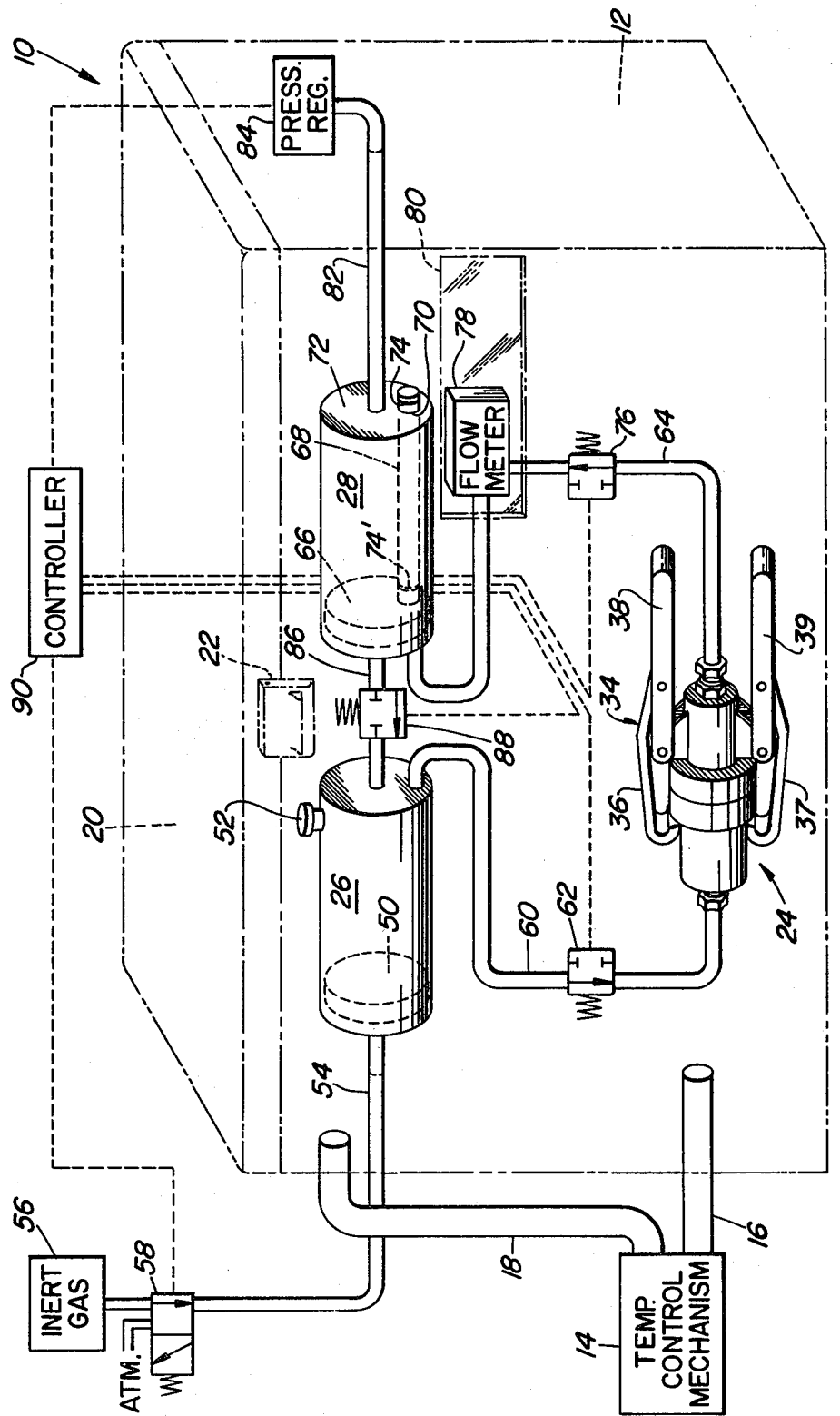
FIG. 1 is an oblique view of the test apparatus positioned with a cold box.

Referring to FIG. 1, an apparatus 10 is shown for measuring the filterability of a fluid at low temperatures. The apparatus 10 includes a cold box 12 which has a temperature control mechanism 14 associated therewith. Two conduits 16 and 18, respectively, route a cooling agent, such as freon, into and out of the cold box 12 so that a desired temperature can be obtained therein. The cold box 12 is an insulated container having a lid 20 which is hinged on one side such that it can be opened or closed relative to the main portion of the box 12. In addition, the cold box 12 has a latch 22 which permits the lid 20 to be securely closed.

The appratus 10 further includes a filter holder 24 fluidly connected between first and second cylinders 26 and 28, respectively. The filter holder 24, best shown in FIG. 2, has a two-part housing 30 and 32, which parts are joined together by a quick attachment and release mechanism 34. As shown in FIG. 2, the quick attachment and release mechanism 34 includes a pair of C-shaped pins 36 and 37 which are attached to overcenter latches 38 and 39, respectively. The operation of such a mechanism is well known to those skilled in the art.

The filter holder 24 is designed to permit the easy insertion or removal of a calibrated ring-shaped filter 40, best shown in FIG. 3. The filter 40 has a central disc of filter media 41 which can be buttressed by screens 42 and 44 on one or both sides. Preferably, the screens 42 and 44 will be placed on both sides of the filter media 41. The screens 42 and 44 are of a much larger mesh than the filter media 41 and do not obstruct the fluid flow passing therethrough. Instead, the screens 42 and 44 serve to support the media 41 and prevent the filter 40 from being displaced within the filter holder 24. This prevents fluid from passing around the periphery of the filter 40. The filter holder 24 also includes a fluid inlet 46 and a fluid outlet 48.

Returning to FIG. 1, the first cylinder 26 contains a free piston 50 and has a closure cap 52 to the right of the piston 50 through which a quantity of fluid can be either inserted into or removed from the cylinder 26. The first cylinder 26 also has a passage 54 which communicates with a non-fluid side of the piston 50 and which conveys an inert gas, such as nitrogen or argon, from a supply source 56. This inert gas is pressurized to a predetermined pressure and is routed to the cylinder 26 via a regulating valve 58 positioned across the passage 54. Preferably, the valve 58 is a two-way valve which opens the passage 54 to the atmosphere when it is in its alternate position. The pressurized gas serves to move the piston 50 and the fluid to the right, without imparting heat into the fluid, as would be the case if a mechanical pump was used.

Extending out of the fluid side of the cylinder 26 is a fluid passage 60 which leads to the inlet 46 of the filter holder 24. Positioned across the passage 60 is a control valve 62 which is normally spring biased to an open position thereby permitting fluid flow through the passage 60. Extending out of the outlet 48 of the filter holder 24 is a fluid passage 64 which communicates with the second cylinder 28. The second cylinder 28 is similar to the first cylinder 26 in that it contains a free piston 66 which has a fluid side and a non-fluid side. As shown in FIG. 1, the fluid side is to the left of the piston 66. Fixed to the non-fluid side of the piston 66 is an indicator rod 68 which extends out of the cylinder 28 through an opening 70 formed in an end wall 72. The indicator rod 68 has at least one and preferably two or more indicating marks, labeled 74 and 74', formed thereof. The indicator marks 74 and 74' indicate the position of the free piston 66 within the second cylinder 28. For example, when the indicator mark 74 is aligned with the outer surface of the end wall 72, the free piston 66 will be in its leftmost position and when the indicator mark 74' is in alignment with the outer surface of the end wall 72, the piston 66 will be in its rightmost position. The indicator rod is only illustrative of one way for indicating the position of the piston 66 and it will be appreciated that those skilled in the art will be aware of other means for indicating the position of the piston 66 within the second cylinder 28. Such alternative arrangements are viewed as part of this invention. The position of the piston 66 directly relates to the amount of fluid which is present in the second cylinder 28.

Positioned across the fluid passage 64, between the filter holder 24 and the second cylinder 28, is a control valve 76 and a flow meter 78. The control valve 76 is spring biased to an open position such as to permit fluid flow through the passage 64. The flow meter 78 is of conventional construction and is capable of measuring the fluid flow through the passage 64. It should be noted that the fluid flow through the passage 64 is the same as the fluid flow across the filter 40. Preferably, the cold box 12 will contain a window 80 through which the operator can read the flow meter 76 and also see the position of the indicator rod 68.

Extending out of the non-fluid side of the second cylinder 28 is a fluid passage 82 which terminates at a pressure regulator 84, positioned outside of the cold box 12. The pressure regulator 84 is a conventional device which can regulate the pressure within the second cylinder 28. The pressure can be set at atmospheric pressure or at a higher or a lower pressure depending upon the test procedure which is to be used. The pressure regulator 84 enables the test operator to create a pressure within the second cylinder 28 such that a back pressure will be present within the filter holder 24. This back pressure will act on the fluid passing through the filter 40 and thus simulate the back pressure which would normally be present in an actual device, such as a full-size engine. The ability of the operator to produce a back pressure within the second cylinder 28 adds a degree of freedom to the test apparatus 10 because a selected pressure differential can be obtained across the filter 40.

The apparatus 10 also includes a return passage 86 located between the fluid sides of the first and second cylinders 26 and 28, respectively, and contains a control valve 88. The control valve 88 is normally spring-biased to a closed position to prevent fluid flow through the return passage 86. When the control valve 88 is opened, fluid from the second cylinder 28 is permitted to flow back into the first cylinder 26 such that the free pistons 50 and 66 will move to the left-hand ends of their respectively cylinders. The ability to return the fluid back to the first cylinder 26 permits an operator to repeat the measurements on a given quantity of fluid thereby checking the accuracy of the previous tests.

It should be noted that the operation of the valves 58, 62, 76, 84 and 88 are controlled by a controller 90 which is positioned outside of the cold box 12. The controller 90 can be of conventional construction having manually operated levers or buttons such that each of the valves can be operated independently of each other.

OPERATION

The method of measuring the filterability of a fluid through a calibrated filter at low temperatures will now be explained starting from a position wherein the pistons 50 and 66 are in their leftmost positions within their respective cylinders 26 and 28. The test operator first inserts a calibrated filter media 41 into the filter holder 24 and then securely joins the two parts 30 and 32 of the housing together. The operator then removes the closure cap 52 on the first cylinder 26 and inserts a predetermined quantity of fluid such that fluid will be present in the passages 60 and 64 and within the fluid portion of the first cylinder 26. It should be noted that it is desirable to insert the fluid into the first cylinder 26 from a vacuum bottle or similar container to assure that no air is trapped therein. Having done the above, the operator will tighten the closure cap 52 and close the lid 20 on the cold box 12. The cold box 12 is then cooled by the temperature control mechanism 14 until a desired temperature value is reached.

For purposes of illustration only, it will be assumed that a back pressure is present within the non-fluid side of the second cylinder 28 and that the pressurized inert gas 56 is at a sufficient pressure so as to move the piston 50 to the right once the valve 58 is moved to a position to permit passage of the gas through the passage 54. As the pressurized inert gas impinges on the left-hand surface of the piston 50, it forces the piston 50 rightward, which in turn forces the fluid out of the first cylinder 26 and through the passage 60. Since the control valve 62 is in an open position, the fluid will flow into the filter holder 24 and through the filter 40. From here the fluid will flow out through the passage 64 to the second cylinder 28. The flow rate of the fluid will be recorded by the flow meter 78.

As the fluid enters the second cylinder 28, it will move the piston 66 to the right against the pressure in the non-fluid side of the cylinder 28. As the piston 66 moves to the right, the indicator rod 68 will move likewise thereby indicating the quantity of fluid which is entering into the second cylinder 28. By recording the amount of time necessary for a predetermined quantity of fluid to flow through the filter at a desired temperature, one is able to calculate the filterability of that particular fluid through a pre-sized filter. When the piston 50 is in its rightmost position within the first cylinder 26, the piston 66 will be in its rightmost position within the cylinder 28. At this point, the operator closes the valves 58, 62 and 76 and opens the control valve 88. By relieving the pressure within the fluid passage 54 via the regulating valve 58 and by supplying a pressure to the right side of the piston 66 via the pressure regulator 84, the piston 66 will move to its left thereby causing the fluid to leave the second cylinder 28 and enter the first cylinder 26. Once both pistons 50 and 566 have reached their leftmost position, the control valve 88 is closed and the valve 62 and 76 are opened. The apparatus is now ready to repeat another cycle.

While this invention has been described in conjunction with a specific embodiment, it is to be understood that many alternatives, modifications, and variations will be apparent to those skilled in the art in light of the aforegoing description. Accordingly, this invention is intended to embrace all such alternatives, modifications, and variations which fall within the spirit and scope of the appended claims.

I claim:

1. An apparatus for measuring the filterability of a fluid at low temperatures, said apparatus comprising:
   (a) a container having a temperature regulating mechanism connected thereto;
   (b) a filter holder enclosed in said container and including a two part housing joined together by a quick attachment and release mechanism, said filter holder having a fluid inlet and a fluid outlet and retaining a filter therebetween;
   (c) a first cylinder containing a free piston and housing a quantity of fluid therein, one end of said first cylinder being connected to said inlet of said filter holder and an opposite end of said first cylinder being connected to a supply of pressurized gas;
   (d) a second cylinder containing a free piston and housing a quantity of a gas, one end of said second cylinder being connected to said outlet of said filter holder and an opposite end of said second cylinder being connected to a pressure regulator;
   (e) a flow meter positioned between said filter holder and said second cylinder for recording fluid flow therebetween; and
   (f) control valves situated on inlet and outlet sides of said filter holder for regulating the flow of said fluid from said first cylinder to said second cylinder.

2. The apparatus of claim 1 wherein a return passage connects said second cylinder to said first cylinder and a control valve is positioned across said return passage for regulating fluid flow therethrough.

3. The apparatus of claim 1 wherein an indicator rod is fixed to one side of said free piston within said second cylinder and extends out of an adjacent end, said indicator rod having at least one mark thereon which when aligned with an outer end of said second cylinder indicates the position of said free piston within said second cylinder.

4. The apparatus of claim 1 wherein said supply of pressurized gas which is connected to said first cylinder and said pressure regulator which is connected to said second cylinder are both positioned outside of said container.

5. The apparatus of claim 1 wherein a screen is positioned upstream of said filter within said filter holder.

6. The apparatus of claim 1 wherein a screen is positioned downstream of said filter within said filter holder.

7. The apparatus of claim 1 wherein a screen is positioned on both sides of said filter within said filter holder.

8. An apparatus for measuring the filterability of a lubricating oil at low temperatures, said apparatus including a cold box having a temperature regulating mechanism connected thereto and further comprising:
   (a) a filter holder including a two part housing joined together by a quick attachment and release mechanism, said filter holder having a fluid inlet and a fluid outlet and retaining a filter therebetween;
   (b) a first cylinder containing a free piston therein and having a port for illing said first cylinder with a quantity of fluid;
   (c) a first passage connecting a fluid side of said free piston within said first cylinder to said inlet of said filter holder;
   (d) a supply of pressurized inert gas positioned outside of said cold box;
   (e) a second passage connecting said supply of pressurized inert gas to a non-fluid side of said free piston within said first cylinder;
   (f) a second cylinder containing a free piston therein and an indicator rod fixed to a non-fluid side of said free piston which extends out of an adjacent end wall of said second cylinder, said indicator rod having at least one mark thereon which when aligned with an outer end surface of said second cylinder indicates the position of said free piston within said second cylinder;
   (g) a third passage connecting said outlet of said filter holder to a fluid side of said second cylinder;
   (h) a flow meter positioned across said third passage for measuring fluid flow therethrough;

(i) a pressure regulator positioned outside of said cold box and connected by a fourth passage to a non-fluid side of said free piston within said second cylinder for maintaining a pressure within said second cylinder;

(j) a fifth passage connecting said fluid side of said second cylinder to said fluid side of said first cylinder; and (k) control valves positioned across said first, second, third and fifth passages for regulating the flow of said fluid therethrough.

9. The apparatus of claim 8 wherein said inert gas is nitrogen.

10. The apparatus of claim 8 wherein said inert gas is argon.

11. A method of measuring the filterability of a fluid at low temperatures with an apparatus which includes a cold box, a filter holder enclosed in said cold box and containing a pre-sized filter media, and a fluid supply cylinder and a fluid receiving cylinder fluidly connected to said filter holder, both of said cylinders having a free piston therein, said method comprising the steps of:

(a) delivering a predetermined quantity of fluid under a preselected pressure and a preselected temperature to said filter media;

(b) measuring the flow of said fluid across said filter media; and (c) recording the time required to pass said predetermined quantity of fluid through said pre-sized filter media thereby measuring the filterability of said fluid at a given temperature.

12. A method of measuring the filterability of a fluid at low temperatures with an apparatus which includes a cold box, a filter holder enclosed in said cold box and being fluidly connected between a fluid supply cylinder and a fluid receiving cylinder, both cylinders having a free piston therein, said method comprising the steps of:

(a) placing a calibrated filter in said filter holder;

(b) filling said supply cylinder and interconnecting passages with a predetermined quantity of a fluid to be tested;

(c) regulating the temperature of said cold box to a desired value;

(d) supplying an inert gas at a selected pressure to a non-fluid side of said free piston within said first cylinder thereby causing said piston to force said fluid contained therein through said filter and into said second cylinder;

(e) measuring the flow of said fluid through said filter; and (f) recording the time required to pass said predetermined quantity of fluid through said filter thereby measuring the filterability of said fluid at a given temperature.

13. The method of claim 12 including the step of supplying a pressure to a non-fluid side of said free piston within said second cylinder thereby creating a back pressure on said fluid passing through said filter to more realistically simulate actual conditions within the lubricating system of an engine.

14. The method of claim 12 including the step of returning said fluid from said second cylinder to said first cylinder through a return passage which bypasses said filter so as to be able to repeat said measurement.

* * * * *

UNITED STATES PATENT AND TRADEMARK OFFICE
CERTIFICATE OF CORRECTION

PATENT NO. : 4,446,726
DATED : 8 May 1984
INVENTOR(S) : Richard L. Hockenberry

It is certified that error appears in the above-identified patent and that said Letters Patent is hereby corrected as shown below:

Column 6, line 46, delete "illing" and insert -- filling --.

Signed and Sealed this

Fifteenth Day of January 1985

[SEAL]

Attest:

GERALD J. MOSSINGHOFF

Attesting Officer

Commissioner of Patents and Trademarks